US009700623B2

(12) United States Patent
Chen et al.

(10) Patent No.: US 9,700,623 B2
(45) Date of Patent: *Jul. 11, 2017

(54) PHARMACEUTICAL COMPOSITION USED FOR REDUCING DAMAGE CAUSED BY FREE RADICALS

(71) Applicant: Original BioMedicals Co., Ltd, Tainan (TW)

(72) Inventors: Chia-Hung Chen, New Taipei (TW); Chau-Hui Wang, New Taipei (TW); John-Son Lin, Taipei (TW); Tieh-Hsiung Chiu, Los Angeles, CA (US); Jing-Yi Chen, Taipei (TW); Pi-Hung Liao, Kaohsiung (TW); Chia-Chi Su, Taichung (TW); Wei-Chuan Liao, Kaohsiung (TW)

(73) Assignee: ORIGINAL BIOMEDICALS CO., LTD., Tainan (TW)

( * ) Notice: Subject to any disclaimer, the term of this patent is extended or adjusted under 35 U.S.C. 154(b) by 370 days.

This patent is subject to a terminal disclaimer.

(21) Appl. No.: 14/348,100

(22) PCT Filed: Nov. 22, 2012

(86) PCT No.: PCT/CN2012/085066
§ 371 (c)(1),
(2) Date: Mar. 28, 2014

(87) PCT Pub. No.: WO2014/079020
PCT Pub. Date: May 30, 2014

(65) Prior Publication Data
US 2015/0290321 A1     Oct. 15, 2015

(51) Int. Cl.
*A61K 47/02*     (2006.01)
*A61K 45/06*     (2006.01)
(Continued)

(52) U.S. Cl.
CPC ............ *A61K 47/02* (2013.01); *A61K 9/1075* (2013.01); *A61K 31/05* (2013.01); *A61K 31/12* (2013.01);
(Continued)

(58) Field of Classification Search
CPC .... A61K 31/661; A61K 31/185; A61K 31/12; A61K 31/198; A61K 31/19; A61K 33/26;
(Continued)

(56) References Cited

U.S. PATENT DOCUMENTS

2007/0248537 A1* 10/2007 Yang .................. A61K 51/0491
424/1.49
2013/0071482 A1* 3/2013 Bae ....................... C09B 69/101
424/497
2013/0131283 A1* 5/2013 Wang ..................... C08G 81/00
525/450

OTHER PUBLICATIONS

Partial English Translation of JP 2011-105792; Translation provided by Steven Spar of the USPTO Translation Service Center, Jul. 29, 2013.*

(Continued)

*Primary Examiner* — Rachael Bredefeld
(74) *Attorney, Agent, or Firm* — WPAT, PC

(57) ABSTRACT

The present invention features a pharmaceutical composition used for reducing the damage caused by free radicals, which comprises at least a metal or its ions, at least a drug or an antioxidant that is carrier-protected/modified, and a drug carrier. Said carrier helps to preserve the anti-oxidative activity, and hence, prevents the decrease of the effect of the antioxidant against free radicals produced in the environment or body fluids and prolongs protection, and may be used for reducing damage caused by radiation and adverse effects induced by chemotherapeutic drugs.

1 Claim, 3 Drawing Sheets

(51) Int. Cl.
*A61K 38/06* (2006.01)
*A61K 31/375* (2006.01)
*A61K 33/34* (2006.01)
*A61K 33/30* (2006.01)
*A61K 33/26* (2006.01)
*A61K 33/24* (2006.01)
*A61K 33/06* (2006.01)
*A61K 31/4045* (2006.01)
*A61K 31/385* (2006.01)
*A61K 31/05* (2006.01)
*A61K 31/355* (2006.01)
*A61K 31/353* (2006.01)
*A61K 31/205* (2006.01)
*A61K 31/198* (2006.01)
*A61K 31/19* (2006.01)
*A61K 31/185* (2006.01)
*A61K 31/122* (2006.01)
*A61K 31/12* (2006.01)
*A61K 9/107* (2006.01)
*A61K 31/661* (2006.01)
*A61K 47/34* (2017.01)

(52) U.S. Cl.
CPC .......... *A61K 31/122* (2013.01); *A61K 31/185* (2013.01); *A61K 31/19* (2013.01); *A61K 31/198* (2013.01); *A61K 31/205* (2013.01); *A61K 31/353* (2013.01); *A61K 31/355* (2013.01); *A61K 31/375* (2013.01); *A61K 31/385* (2013.01); *A61K 31/4045* (2013.01); *A61K 31/661* (2013.01); *A61K 33/06* (2013.01); *A61K 33/24* (2013.01); *A61K 33/26* (2013.01); *A61K 33/30* (2013.01); *A61K 33/34* (2013.01); *A61K 38/063* (2013.01); *A61K 45/06* (2013.01); *A61K 47/34* (2013.01)

(58) Field of Classification Search
CPC ........ A61K 33/24; A61K 47/02; A61K 47/34; A61K 45/06; A61K 9/1075
See application file for complete search history.

(56) References Cited

OTHER PUBLICATIONS

Santini, "Amifostine: chemotherapeutic and radiotherapeutic protective effects," Expert Opinion on Pharmacotherapy, 2001, 2(3), pp. 479-489.*

* cited by examiner

PHARMACEUTICAL COMPOSITION USED FOR REDUCING DAMAGE CAUSED BY FREE RADICALS

BACKGROUND OF THE INVENTION

1. Field of the Invention

The present invention relates to a pharmaceutical composition, in particular, a pharmaceutical composition that reduces damage caused by free radicals.

2. Description of the Prior Art

Amifostine, also called WR-2721, is the prodrug of WR-1065 with phosphate groups, and exhibits antioxidative activity. At present, drug regulatory agencies in many countries have approved the use of amifostine as a radioprotective drug for treating damage caused by radiation therapy, and the adverse effects induced by platinum-related chemotherapeutic drugs. Amifostine is spontaneously hydrolyzed in vivo, or metabolized by alkaline phosphatase through breaking up the bond between WR-1065 and its phosphate groups. The active drug, WR-1065, is then released and protects cells from damage and reduces cell toxicity by scavenging free radicals. Nonetheless, studies in patients have indicated that the distribution half-life of amifostine is less than 1 minute, and the elimination half-life is 8 minutes. Only 10% of amifostine remains 6 minutes after i.v. injection. Un-eliminated amifostine is rapidly converted to active free thiol metabolite, WR1065, and starts to function. Therefore, clinically amifostine is usually administered through i.v. injection 3 and 15 minutes before radiation therapy and chemotherapy, respectively. As a result, the most difficult problem facing the clinical application of amifostine is its short half-life.

Numerous studies and literatures have suggested that amifostine can be formulated as a slow-release or non-parenteral administration drug. Although oral administration of such formulated amifostine has been reported to prolong its half-life and increase its efficacy, none have shown better results in treating various clinical complications such as the prevention of radiation toxicity caused by nuclear plant explosion or accidental exposure, simply because no effective methods are available to control the release and selective distribution of amifostine in radio-sensitive tissues and organs.

In addition, other antioxidants may not provide long-term protection against free radicals either because it is difficult to maintain their potency or easily to be metabolized in vivo. Thus, these antioxidants may not be easily applied for protection of normal tissue from damage caused by radiation toxicity or chemotherapy.

SUMMARY OF THE INVENTION

Based upon the aforementioned background information and in meeting the special requirements in the industry, the present invention uses the metal ion composition technology as disclosed in our prior invention (Taiwan Patent Application Number 101128939) to encapsulate amifostine or other antioxidants in metal ion-containing micelle and use it for reducing damage caused by radiation toxicity and chemotherapy. This pharmaceutical composition can prolong the half-life of these drugs, protect the drug activities, and alter the distributions of the drugs in vivo. Moreover, the said pharmaceutical composition of the present invention can delay the drug release profiles and change drug distribution in vivo, which consequently reduces damage cause by radiation and adverse effects induced by chemotherapeutic drugs. The pharmaceutical composition may be designed according to different requirements including lipophilicity and particle size so as to ensure distribution at target organs resulting in the protection of the tissue and organ.

The active ingredients released from the pharmaceutical composition such as amifostine, WR1065, or other antioxidants can reduce damage in the normal tissues induced by free radicals during radiation therapy or chemotherapy and consequently reduce radical induced toxicity.

The goal of the present invention is to provide a pharmaceutical composition for reducing damage caused by free radicals. The composition includes at least one metal or its ion, at least one drug or one carrier-protected and modified antioxidant, and a drug carrier.

To accomplish the goal of the present invention, the metal core of the aforementioned micelle is selected from one of the following metals or their combinations and/or their derivatives thereof: Fe, Cu, Ni, In, Ca, Co, Cr, Gd, Al, Sn, Zn, W, Sc, and Ti.

In addition, the drug carrier of the composition is selected from one of the following groups or their combinations and/or their derivatives thereof: Poly(ethylene glycol), poly(aspartic acid), poly(glutamic acid), polylysine, poly(acrylic acid), chitosan, polyethyleneimine, poly(methacrylic acid), hyaluronic acid, collagen, poly(N-isopropyl acrylamide), amylose, cellulose, poly hydroxybutyrate, poly(lactic acid), poly(butylene succinate), poly(caprolactone), carboxymethylcellulose, dextran, cyclodextrin, Poly(ethylene glycol)-b-poly(glutamic acid) and phospholipid.

Moreover, the aforementioned drug carrier is selected from one of the following groups or their combinations thereof: liposome, micelle/polymeric micelle and dendrimer.

The pharmaceutical composition of the present invention is either bond or not bond with a metal, and the drug contained is selected from one of the following or their combinations and/or derivatives thereof: amifostine, WR-1065, ascorbic acid (Vitamin C), glutathione, melatonin, tocopherols, tocotrienol (Vitamin E), L-carnitine, carotenes, ubiquinol, lipoic acid, polyphenols, catecholamine, curcumin, resveratrol, piceid, acetylcysteine, tempo, asarone, aminoguanidine, tocopherol monoglucoside, glycyrrhizic acid, epicatechin, flavonoid, orientin, vicenin, MPG (2-mercaptopropionyl glycine), and Mesna (2-mercaptoethanesulfonic acid).

A pharmaceutical composition used for reducing the damage caused by free radicals, comprising Iron ion, amifostine, and a drug carrier; wherein said the drug carrier is poly(ethylene glycol)-b-poly(glutamic acid) (PEG-b-PGA).

In another aspect, the said pharmaceutical composition can be utilized as a reducing agent to reduce the oxidized biomolecules and restore their functions by blocking the continuous transmission and attacks of free radicals; therefore, could reduce the level of free radicals produced by radiation, ultraviolet light, chemotherapeutic drugs and electromagnetic effects so as to prevent damage caused by free radicals and reduce the resulted toxicity.

BRIEF DESCRIPTION OF THE DRAWINGS

The foregoing summary, as well as the following detailed description of the invention, will be better understood when read in conjunction with the appended drawings. It should be understood, however, that the invention is not limited to the preferred embodiments shown.

DETAILED DESCRIPTION OF THE PREFERRED EMBODIMENT

The present invention will now be described more specifically with reference to the following embodiments, which are provided for the purpose of demonstration rather than limitation.

EXAMPLE 1

Formulation of the Controlled-release Drug Carrier of the Pharmaceutical Composition with a Metal Core.

Figure 1:
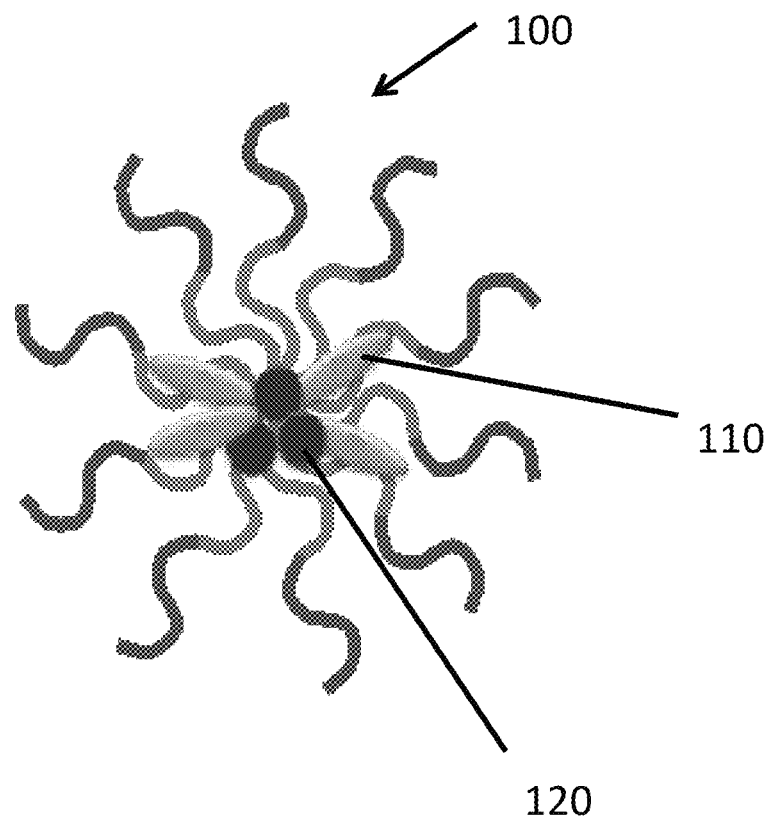
FIG. 1 is a schematic diagram of the pharmaceutical composition with a metal core according to Example 1 of the present invention. ***P<0.001 significant differences from UV group. #P<0.05 significant differences from API 40×2 h group. ▲▲▲P<0.001 significant differences from FePA 20×2 h group.

FIG. 1 is a schematic diagram of the pharmaceutical composition with a metal core. The center consists of a metal or metal ions 120 and is enclosed by an antioxidant compound or other similar drug(s) 110, and the outer layer is made of drug carrier 100.

Active Substances

Amifostine is an antioxidant and a derivative of WR-1065 conjugating with phosphate groups, which exhibits antioxidative activity. Amifostine is currently approved by regulatory agencies in many countries for preventing radiation toxicity and adverse effects induced by cisplatin-like chemotherapeutic drugs.

The Drug Carrier for the Pharmaceutical Composition

Fifteen gram of γ-benzyl-L-glutamate and 7.5 g triphosgene were dissolved in tetrahydrofuran (THF) and stirred at 55° C. in the presence of $N_2$ till the solution is clear. Following concentration of the solution, 400 mL n-hexane was used for precipitation. The monomer, N-carboxy-γ-benzyl-L-glutamate anhydride (BLG-NCA), is obtained after removal of n-hexane with 300 mL n-hexane/ethyl acetate (1/1) and crystallization. Fifteen grams of BLG-NCA and 2.1 g α-amino-ω-methoxy-poly(ethylene glycol) (PEG-$NH_2$) were dissolved in 43 mL dimethyl sulfoxide (DMSO) and stirred at 40° C. for 72 hrs. The crude product was then subjected to precipitation using 215 mL diethyl ether followed by removal of diethyl ether, and 315 mL ethanol and 210 mL 1N NaOH were then added and the mixture stirred at 25° C. for 24 hrs. The pH value was adjusted to 7.0 by adding 35% HCl on ice, and then purified using MWCO 3500 membrane by dialysis. Poly(ethylene glycol)-b-poly(glutamic acid) (PEG-b-PGA) is then obtained after freeze-drying (lyophilization).

The present invention provides a material, and said material contains 206.44 mg Amifostine, 825.50 mg PEG-b-PGA and 206.44 mg Iron (II) chloride ($FeCl_2.4H_2O$). The obtained material was then added to 41.288 ml HEPES buffer [4-(2-hydroxyethyl)-1-piperazinee-thanesulfonic acid)] and stirred vigorously on a shaker at 200 rpm with the pH at 7.0 at 25 degree Celsius (° C.).

Formulation of FePA is based on the ratio of PEG-b-PGA: $FeCl_2.4H_2O$:amifostine=4:1:1 (w:w:w, according to the ratios of weight) with a preferred amifostine concentration at 5 mg/mL. Accordingly, the material containing amifostine is formed by self-assembly of ferrous ion ($Fe^{2+}$) and PEG-b-PGA via coordinate bonding.

FORMULATION EXAMPLE 1 (FePA)

| | |
|---|---|
| Amifostine | 206.44 mg |
| PEG-b-PGA | 825.50 mg |
| Iron(II) chloride | 206.44 mg |
| Total: | 1238.38 mg |

In Vitro Antioxidative Activities of the Pharmaceutical Composition with a Metal Nucleus UV irradiation of the cells was used in this experiment to simulate the effects of radiation on normal cells, and the results were evaluated by Comet Assay. Comet Assay is a fast, sensitive and convenient method for examining DNA damage and is widely used in studying DNA damage caused by radiation, examining DNA crosslink, evaluating genotoxicity of drugs and identifying cell apoptosis, etc.

In total, eight groups were included in this experiment:
API group received 1 mg/mL amifostine;
FePA group received 1 mg/mL $FeCl_2.4H_2O$, 4 mg/mL PEG-b-PGA and 1 mg/mL amifostine;
FeP group received 1 mg/mL $FeCl_2.4H_2O$ and 4 mg/mL PEG-b-PGA The animals in each test group received 1 mL of the treatment drug(s) and the corresponding treatment methods are shown as follows:

TABLE 1

| Group name | Number of dish | Treatment condition |
|---|---|---|
| CON | 2 | No UV irradiation and no treatment |
| UV | 2 | UV irradiation without treatment |
| API 40x | 2 | Drug added 2 hr prior to UV irradiation |
| API 40x | 2 | Drug added 30 min prior to UV irradiation |
| FeP 40X | 2 | Drug added 2 hr prior to UV irradiation |
| FePA 20x | 2 | Drug added 2 hr prior to UV irradiation |
| FePA 20x | 2 | Drug added 30 min prior to UV irradiation |

CON: Negative Control
UV: UV irradiation without drug treatment as Positive Control as Positive Control
40X: 40 folds dilution with PBS
20X: 20 folds dilution with PBS The mouse embryonic liver cells (BNLCL.2) were inoculated onto a 35 mm culture dish at the density of $3*10^5$ cell/mL and cultured for at least 20 hr before subjected to the test. After removal of supernatant, fresh medium containing serum and various test compounds was added to the control and the test groups at different times according to the experimental design. The culture dish was then washed with PBS and irradiated with UVB (100 J·m-2 UVB doses). Next, 2 mL fresh medium added, and the treated cells were cultured in the incubator for 4 hr to allow the drugs to take effects. The treated cells were then collected with a scraper, counted, and centrifuged at 1,200 rpm for 5 minutes. Followed by washing with PBS ($Ca^{2+}$, $Mg^{2+}$ free) once, the cell number was adjusted to $1*10^5$ cell/mL by adding PBS.

The bottle containing LM agarose was placed in 95° C. water for 5 minutes with loosed cap and then transferred to a 37° C. water bath for at least 20 minutes. The cells ($1\times10^5$/ml) and melted LM agarose were combined in the volume of 7 µL and 70 µL, respectively, at 37° C., and 60 µL mixture was immediately spread on a CometSlide™ and allowed to set flat on ice for 10 minutes and protected from light. At the end of incubation, the slide was immersed in pre-cooled Lysis buffer and stored at 4° C. for 30 minutes. The excess buffer on the slide was removed by gently tapping, and then placed in freshly prepared Alkaline Unwinding Solution at room temperature for 60 minutes and protected from light. Later, 950 mL pre-cooled Alkaline Electrophoresis Solution was added to the electrophoresis tank followed by placement of the slide in the tank and covered with slide Tray Overlay. The electrophoresis conditions are 21 V for 30 minutes. At the end of electrophoresis, the solution was gently removed and the slide was immersed first in de-ionized water twice for 5 minutes each time; and then in 70% ethanol for additional 5 minutes. The slide sample was then air-dried in the hood to allow easy observation of the single plane view of the cells. The sample can be stored at room temperature at this step with desiccant or proceed to the next step directly. An aliquot of 100 µL diluted SYBR Green I was added to dried gel and stored at 4° C. for 5 minutes. Excess SYBR solution was removed from the slide by gently tapping and air-dried at room temperature and protected from light. The resulting images were analyzed using the epifluorescence microscope (the maximum excitation and emission wavelength of SYBR® Green I are 494 nm and 521 nm, respectively.) The fluorescence filter was also adjusted accordingly for efficient lighting) 200×.

Figure 2:
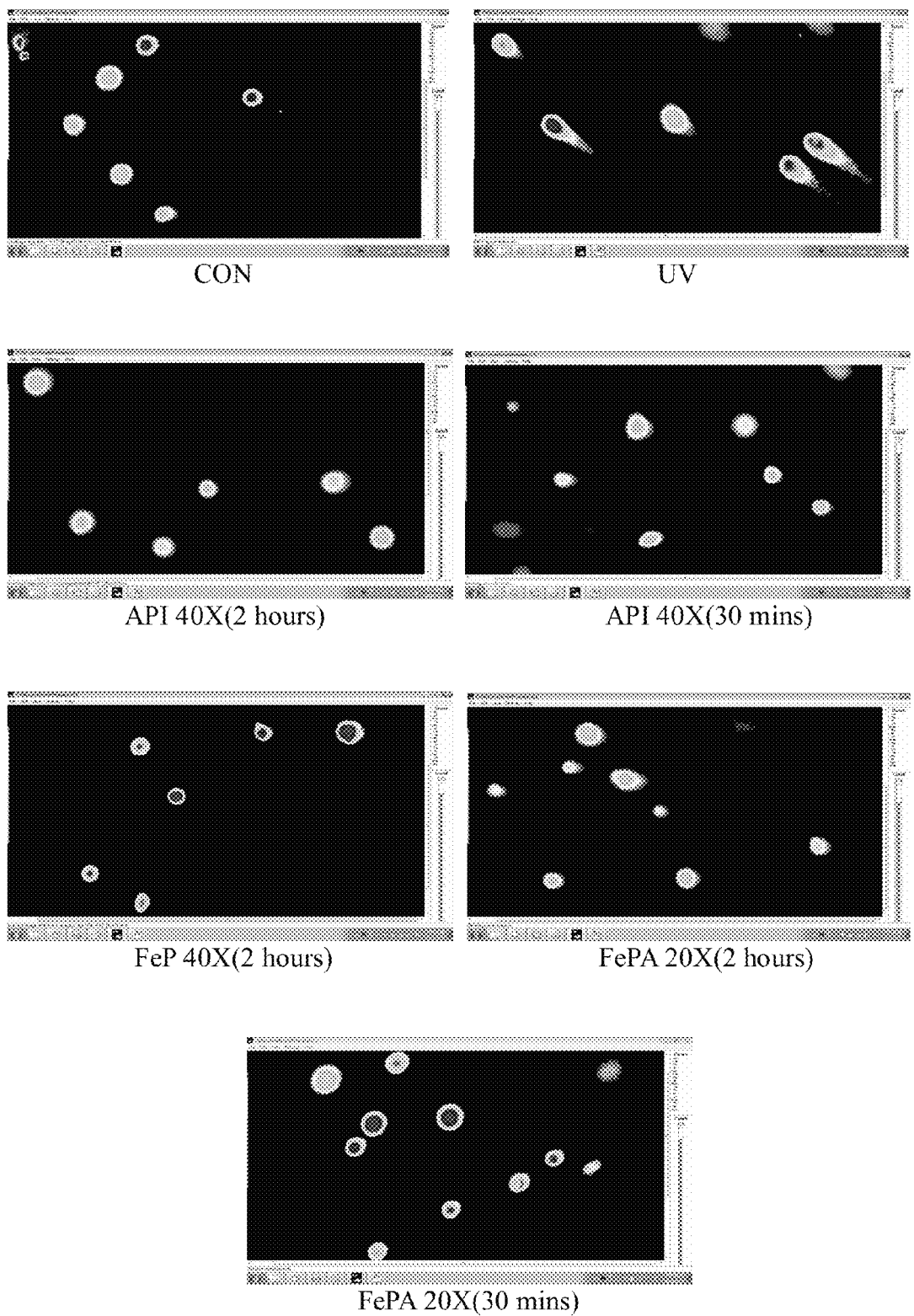
FIG. 2 is image of Comet Assay. CON is negative control, UV is UV irradiation without drug treatment as positive control, API 40×(2 hours), API 40×(30 mins), FeP 40×(2 hours), FePA 20×(2 hours) and FePA 20×(30 mins)
Figure 3:
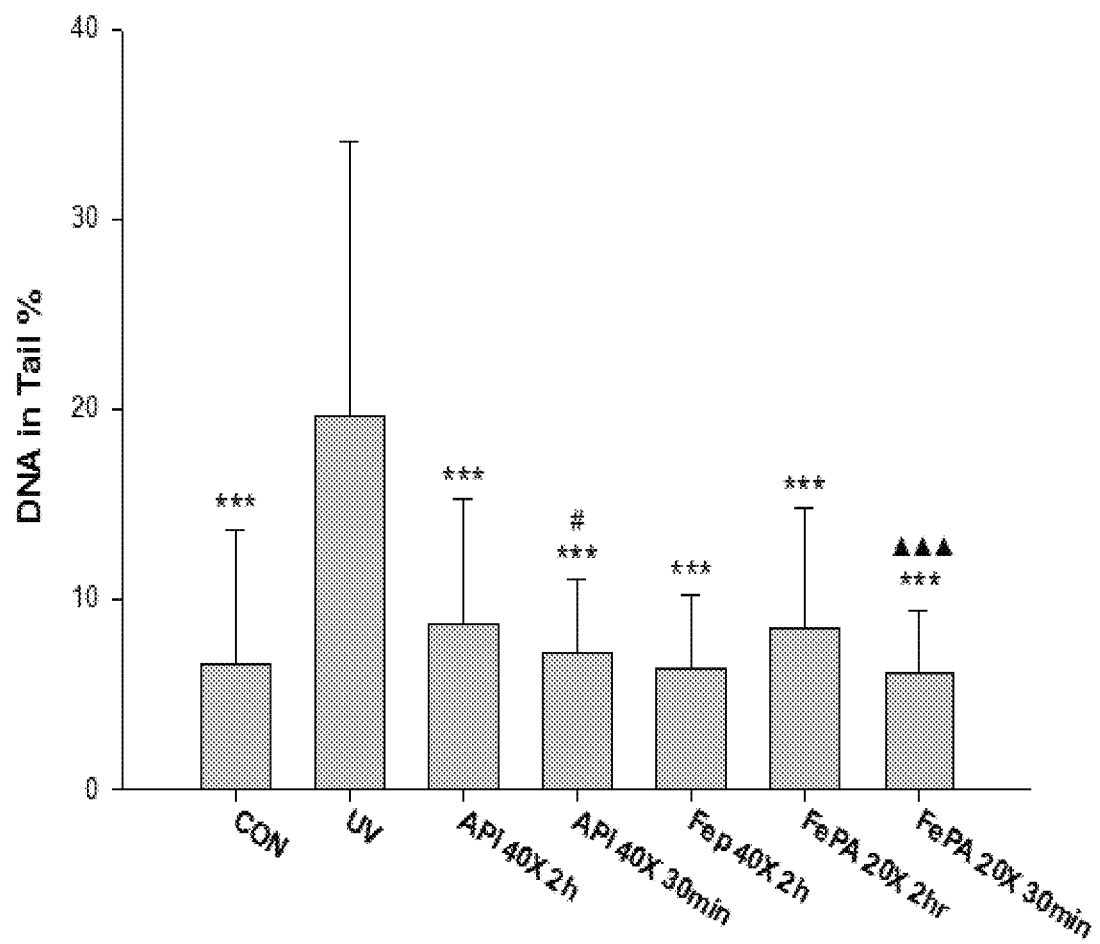
FIG. 3 is a quantitative diagram of Comet Assay DNA in tail(%). CON is negative control, UV is UV irradiation without drug treatment as positive control, API 40×(2 hours), API 40×(30 mins), FeP 40×(2 hours), FePA 20×(2 hours) and FePA 20×(30 mins)

The results are shown in FIGS. 2-3. Compared with the positive control group (UV), the average percentage of damaged DNA in the tail of the Comet (% TDNA) of the FePA20x, API 40x, FeP 40x or group were all significantly reduced when the treatment was given either 30 minutes or 2 hr before UV irradiation. However, the in-vitro experiment was not with sensitivities enough to show the different between drug carrier and API. Thus, administration of FePA indeed protected cells from damage caused by UV irradiation and the treated cells were almost morphologically identical to normal cells without UV irradiation.

Other In Vivo Results Showing Improvements after Radiation Toxicity and Chemotherapy-induced Adverse Effects Efficacy Result In animal study, 30-day old NMRI mice weighing 20 to 30 g were tested for acute radiation protection. For radiation control group, mice were given 1, 4, and 8 Gy irradiation in 10 minutes, and for the standard treatment group, FDA-approved amifostine (6.25 mg/kg) was injected intravenously, and 30 minutes later the animals were given 8 Gy irradiation in 10 minutes. The 30 mins duration design is based on the short half-life of amifostine. A-01 indicates FePA with a formulation ratio of PEG-b-PGA:$FeCl_2 \cdot 4H_2O$:amifostine=4:1:1 (w:w:w). The animals in the test group A-01 were administered intravenously with 37.5 mg/kg A-01 (containing the same amount of amifostine as used in the standard treatment group), and 120 minutes post injection, the animals were given 8 Gy radiation in 10 minutes. WBC number and survival rates were analyzed 30 days after treatment.

As shown in Table 2, WBC numbers in A-01 group were 3 to 4 times more than radiation control group, which suggests that drug A-01 can protect hematopoietic system from damage for at least 2 hr and can significantly reduce infection induced by radiation. Additionally, A-01 contains 6.25 mg/kg amifostine, which suggests that about 30 mg amifostine (equivalent to 180 mg of the said pharmaceutical composition) is effective in providing radiation protection for a 60 kg body weight human Amifostine, approved by the FDA and used in radiation therapy for head and neck tumor, must be administered 3 minutes prior to radiation therapy and only provides obvious protection for salivary gland. The dosage of amifostine required 200 mg/$m^2$ translates to 320 mg amifostine for a 60 kg human. Thus, A-01 drug can provide better protection against radiation toxicity by selective accumulation and slow release.

TABLE 2

| WBC 1000/$cm^3$ | 1Gy | 4Gy | 8Gy | Normal |
|---|---|---|---|---|
| Control | 1.90-1.92 | 1.44-1.84 | 0.54-0.68 | 2.72-3.54 |
| Amifostine (~30 min) | — | — | 3.04-3.80 | — — |
| A-01(~2 hrs) | — | — | 1.66-2.08 | — — |

(— indicates radiation dosage is not enough to produce severe damage in the hematopoietic system; therefore, no drug is administered)
(— — group indicates no adverse effects were observed in either rats or mice in the acute toxicity test and the results are within the normal range, hence WBC counts were not shown)

In conclusion, the present invention provides a metal ion based micelle technology to encapsulate amifostine or other antioxidants so as to reduce the damage caused by radiation and adverse effects induced by chemotherapy. Many changes and modifications in the above described embodiments of the invention can, evidently, be carried out to better control both the release and selective distribution of amifostine in vivo, and thus enhance the drug effects. Accordingly, to promote the progress in science and useful arts, the invention disclosed and the scope of the appended claims are submitted for approval.

What is claimed is:

1. A pharmaceutical composition used for reducing damage caused by free radicals, comprising:
   iron;
   amifostine; and
   poly(ethylene glycol)-b-poly(glutamic acid)
   wherein the pharmaceutical composition is formed by self-assembly of the iron and poly(ethylene glycol)-b-poly(glutamic acid) via coordinate bonding, the center of the pharmaceutical composition consists of the iron and is enclosed by amifostine, and an outer layer is made of the poly(ethylene glycol)-b-poly(glutamic acid).

* * * * *